United States Patent [19]

Shen et al.

[11] 4,368,190
[45] Jan. 11, 1983

[54] IMMUNOLOGICALLY ACTIVE DIPEPTIDYL 4-O-,6-O-ACYL-2-AMINO-2-DEOXY-D-GLUCOSE DERIVATIVES AND METHODS FOR THEIR PREPARATION

[75] Inventors: Tsung-Ying Shen, Westfield; Philippe L. Durette, New Providence; Conrad P. Dorn, Jr., Plainfield; James B. Doherty, New Milford; Richard T. Dean, Fanwood, all of N.J.

[73] Assignee: Merck & Co., Inc., Rahway, N.J.

[21] Appl. No.: 141,227

[22] Filed: Apr. 17, 1980

[51] Int. Cl.³ ............... A61K 37/02; A61K 39/00; C07C 103/52
[52] U.S. Cl. .................. 424/88; 260/112.5 R; 424/177
[58] Field of Search ............... 424/177, 88–92, 424/85; 260/112.5 R

[56] References Cited

U.S. PATENT DOCUMENTS 4,082,735  4/1978  Jones et al. ............ 260/112.5 R
4,082,736  4/1978  Jones et al. ............ 260/112.5 R

FOREIGN PATENT DOCUMENTS 834753   2/1976  Belgium .
834754   2/1976  Belgium .
2677    12/1978  European Pat. Off. .
5682     5/1979  European Pat. Off. .
52-2046020 4/1977  Japan .
54-4130517 10/1979 Japan .
1498394  1/1978  United Kingdom .

OTHER PUBLICATIONS

Ellouz et al., Biochem. Biophys. Res. Commun., 59, 1317–1325 (1974).
Adam et al., Biochem. Biophys. Res. Commun., 72, 339–346 (1976).
Kotani et al., Biken Journal, 18, 105–111 (1975).
Derwent Abstracts, Belgium Pat. No. 852,348 (1977).
Derwent Abstracts, Belgium Pat. No. 852,349 (1977).
Derwent Abstracts, Japanese Pat. No. 2083506 (1977).
Derwent Abstracts, Japanese Pat. No. 2156812 (1977).
Derwent Abstracts, Japanese Pat. No. 3077011 (1978).
Derwent Abstracts, Belgium Pat. No. 834,753 (1976).
Tommasini et al., Arzneimi Forsch., vol. 16, No. 2, pp. 164–174 (1966).

Primary Examiner—Blondel Hazel
Attorney, Agent, or Firm—Donald J. Perrella; Raymond M. Speer; Hesna J. Pfeiffer

[57] ABSTRACT

Immunologically active compounds of the formula:

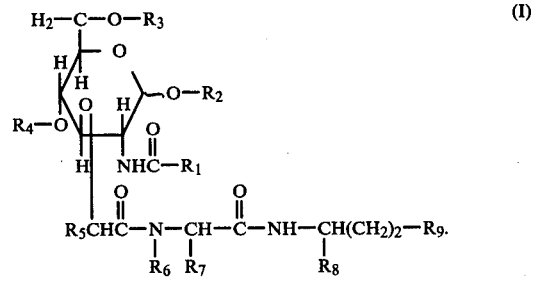

wherein:

$R_1$ is $C_{1-7}$ alkyl; substituted $C_{1-7}$ alkyl; phenyl; or substituted phenyl;

$R_2$ is hydrogen; $C_{1-7}$ alkyl; substituted $C_{1-7}$ alkyl; phenyl; substituted phenyl; phenyl $C_{1-4}$ alkyl; or substituted phenyl $C_{1-4}$ alkyl;

$R_3$ and $R_4$ may be the same or different and are each independently hydrogen, provided that $R_3$ and $R_4$ may not both be hydrogen; or

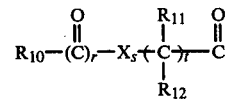

where
X is —O—; —S—; or

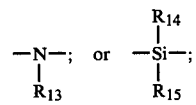

$R_{10}$ is hydrogen; $C_{1-30}$ alkyl; $C_{2-30}$ alkenyl; $C_{1-30}$ alkoxy; phenyl; $C_{1-20}$ alkylsulfonyl; or cholesteryl;

$R_{11}$, $R_{12}$, $R_{13}$, $R_{14}$, and $R_{15}$ may be the same or different and are each independently hydrogen; $C_{1-20}$ alkyl; $C_{1-20}$ alkylcarbonyloxy; amino; benzyl; $C_{1-20}$ alkoxymethyl; $C_{1-20}$ alkylamido; or

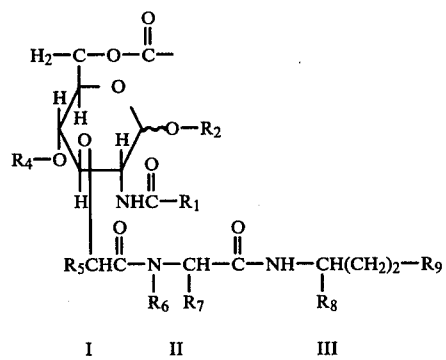

r is 0 or 1; s is 0 or 1; and t is 0 to 20; provided that s may only be 0 when both r and t are greater than 0 or when r is 0 and $R_{10}$ is amino; phenyl; substituted phenyl; 1-adamantyl; or heterocycle selected from the group consisting of 2- or 3-furyl, 2- or 3- thienyl, 2- or 3- pyrrolidinyl, 2-, 3- or 4- pyridyl, and 1-tetrazolyl, said heterocycle optionally substituted with $C_{1-20}$ alkylcarbonyl; and where $R_3$ or $R_4$ is other than hydrogen, the other of $R_3$ and $R_4$ may additionally be $C_{1-4}$ alkylcarbonyl;

$R_5$ is hydrogen or $C_{1-10}$ alkyl;

$R_6$ is hydrogen or $R_6$ and $R_7$ taken together are $-(CH_2)_3-$;

$R_7$ is hydrogen; $C_{1-7}$ alkyl; hydroxymethyl; mercaptomethyl; benzyl; or substituted benzyl;

$R_8$ and $R_9$ may be the same or different and are each independently COOR, or CONR'R'', where R is hydrogen or $C_{1-7}$ alkyl, and R' and R'' are hydrogen or $C_{1-3}$ alkyl;

when $R_5$ is $C_{1-10}$ alkyl, the stereochemistry at asymmetric center I is D or L;

when $R_7$ is other than hydrogen, the stereochemistry at asymmetric center II is L; and the stereochemistry at asymmetric center III is D; and acid addition and quaternary salts thereof.

34 Claims, No Drawings

IMMUNOLOGICALLY ACTIVE DIPEPTIDYL 4-O-,6-O-ACYL-2-AMINO-2-DEOXY-D-GLUCOSE DERIVATIVES AND METHODS FOR THEIR PREPARATION

BACKGROUND OF THE INVENTION

1. Field of the Invention

The present invention is concerned with improved novel immunoadjuvants.

As is known in the field of immunology, multiple injections of a vaccine may be necessary to induce an immune response in a host sufficient to provide immunity because the viral or bacterial antigen contained in the vaccine is often cleared from the injection site too rapidly to permit an adequate immune response. Thus, immunological adjuvants have been added to vaccines in order to delay release of the viral or bacterial antigen and/or to stimulate the host's immunological response. However, many of the earlier immunological adjuvants which were employed had serious drawbacks, such as causing irritation at the site of injection. Accordingly, the art has long sought an immunological adjuvant which would be readily metabolized by the host without serious side effect, while at the same time delaying release of antigen and stimulating the immune response of the host.

One of the most active immunoadjuvants is Freund's Complete Adjuvant which is a water-in-oil emulsion consisting of 10% Arlacel A and 90% mineral oil containing whole killed mycobacterial cells. A vaccine is formulated with Freund's Complete Adjuvant by incorporating the antigen in the aqueous phase. Therapeutic applications of Freund's Complete Adjuvant, however, have been prevented due to accompanying toxic side effects such as local granulomas, endotoxic shock, and adjuvant-induced polyarthritis. The minimal active structure of mycobacteria has been determined by Ellouz et al., *Biochem. Biophys. Res. Commun.*, 59, 1317 (1974) and by Kotani et al., *Biken J.*, 18, 105 (1975) to be a peptidoglycan fragment of the cell wall, more specifically, a muramyl dipeptide, namely, N-acetylmuramyl-L-alanyl-D-isoglutamine (MDP). The addition of synthetic MDP to an emulsion of Freund's incomplete adjuvant (90% mineral oil and 10% Arlacel A) containing an antigen increases the level of antibodies against the antigen (humoral response) and induces delayed hypersensitivity (cellular immunity).

2. Brief Description of the Prior Art

Ellouz et al., *Biochem. Biophys. Res. Commun.*, 59, 1317–25 (1974) discloses that MDP is the minimal bacterial cell wall fragment having adjuvant activity.

Adam et al., *Biochem. Bioyphys. Res. Commun.* 72 339–346 (1976) discloses various lactyl dipeptide modifications of MDP. All were less active than MDP except N-acetyl-muramyl-L-seryl-D-isoglutamine which was as active as MDP.

Kotani et al., *Biken Journal,* 18, 105–111 (1975) discloses that MDP has adjuvant activity in saline solution as well as in water-in-oil emulsion.

U.S. Pat. Nos. 4,082,735 and 4,082,736 disclose various MDP analogs obtained by acetylating the sugar hydroxyl groups, varying the amino acid constituents of the dipeptides, using alkyl or aryl amide substituents, and varying the acid ether linkage between the sugar and the dipeptide.

Belgian Pat. Nos. 852,348 and 852,349 disclose N-acetylmuramyl dipeptides wherein the dipeptide is either L-alanyl-D-isoglutamine or L-seryl-D-isoglutamine, and their esters and amides.

Japanese Pat. Nos. 2083506 and 2046020 disclose N-acetylmuramyl dipeptides acylated with fatty acids at the 6-position of the sugar moiety.

Japanese Pat. No. J5-2156-812 discloses MDP acetylated in the 6-position with mycolic acid.

Japanese Pat. No. J5-3077-011 discloses an analog of the preceding compound wherein glycine is substituted for L-alanine in the dipeptide moiety.

Belgian Pat. Nos. 834,753 and 834,754 disclose oil-free adjuvant compositions containing MDP and an MDP analog wherein D-glutamic acid is substituted for D-isoglutamine.

European Pat. No. 2677 discloses glucosaminepeptide homopolymers and copolymers based on 6-O-MDP derivatives and analogs used as immunostimulating agents.

European Pat. No. 5682 discloses silylglucosamines which are antigens bonded to muramyl peptide derivatives wherein the 4-O- and 6-O- positions are substituted with tri-(lower alkyl)-silyl.

Japanese Pat. No. 54-130,517 discloses MDP higher fatty acid esters in which the 6-O-position is substituted with $C_{1-90}$ acyl, optionally unsaturated, branched, or substituted, and optionally containing additional hydroxyl, carboxyl, carbonyl, amino, methoxy, or cyclopropyl functional groups.

British Pat. No. 1,498,394 discloses behenate esters of thiazanthene derivatives with long-lasting neuroleptic activity.

Tommasini et al., *Arzneimi. Forsch.,* Vol. 16, No. 2, pp. 164–174 (1966), discloses the improved pharmacological activity of prednisolone-21-stearoylglycolate.

SUMMARY OF THE INVENTION

In accordance with the present invention there are provided novel compounds of the formula:

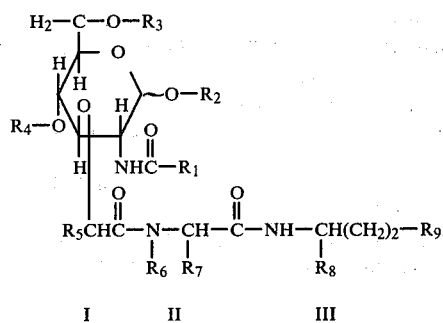

wherein:

$R_1$ is $C_{1-7}$ alkyl; substituted $C_{1-7}$ alkyl; phenyl; or substituted phenyl;

$R_2$ is hydrogen; $C_{1-17}$ alkyl; substituted $C_{1-7}$ alkyl; phenyl; substituted phenyl; phenyl $C_{1-4}$ alkyl; or substituted phenyl $C_{1-4}$ alkyl;

$R_3$ and $R_4$ may be the same or different and are each independently hydrogen, provided that $R_3$ and $R_4$ may not both be hydrogen; or

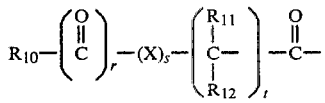

where
X is —O—; —S—; or

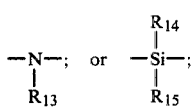

$R_{10}$ is hydrogen; $C_{1-30}$ alkyl; $C_{2-30}$ alkenyl; $C_{1-30}$ alkoxy; phenyl; $C_{1-20}$ alkylsulfonyl; or cholesteryl;

$R_{11}$, $R_{12}$, $R_{13}$, $R_{14}$, and $R_{15}$ may be the same or different and are each independently hydrogen; $C_{1-20}$ alkyl; $C_{1-20}$ alkylcarbonyloxy; amino; benzyl; $C_{1-20}$ alkoxymethyl; $C_{1-20}$ alkylamido; or

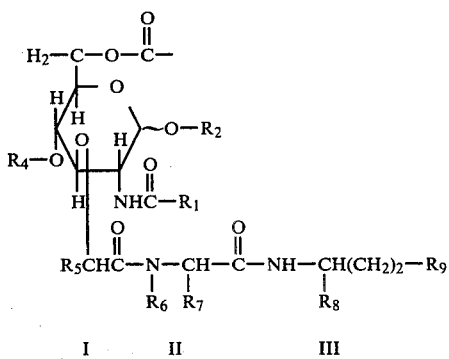

r is 0 or 1; s is 0 or 1; and t is 0 to 20; provided that s may only be 0 when both r and t are greater than 0 or when r is 0 and $R_{10}$ is amino; phenyl; substituted phenyl; 1-adamantyl; or heterocycle selected from the group consisting of 2- or 3-furyl, 2- or 3-thienyl, 2- or 3-pyrrolidinyl, 2-, 3- or 4-pyridyl, and 1-tetrazolyl, said heterocycle optionally substituted with $C_{1-20}$ alkylcarbonyl; and where $R_3$ or $R_4$ is other than hydrogen, the other of $R_3$ or $R_4$ may additionally be $C_{1-4}$ alkylcarbonyl;

$R_5$ is hydrogen or $C_{1-10}$ alkyl;

$R_6$ is hydrogen or $R_6$ and $R_7$ taken together are —$(CH_2)_3$—;

$R_7$ is hydrogen; $C_{1-7}$ alkyl; hydroxymethyl; mercaptomethyl; benzyl; or substituted benzyl;

$R_8$ and $R_9$ may be the same or different and are each independently COOR, or CONR'R", where R is hydrogen or $C_{1-7}$ alkyl, and R' and R" are hydrogen or $C_{1-3}$ alkyl;

when $R_5$ is $C_{1-10}$ alkyl, the stereochemistry at asymmetric center I is D or L;

when $R_7$ is other than hydrogen, the stereochemistry at asymmetric center II is L; and the stereochemistry at asymmetric center III is D; and acid addition and quaternary salts thereof.

Particularly preferred compounds of the present invention are the following:

2-acetamido-6-O-behenoyloxyisobutyryl-2-deoxy-3-O-(D-2-propionyl-L-alanyl-D-isoglutamine)-D-glucose 2-acetamido-2-deoxy-6-O-(N,O-dipalmitoyl-D,L-seryl)-3-O-(D-2-propionyl-L-alanyl-D-isoglutamine)-D-glucose 2-acetamido-6-O-(adamantane-1-carbonyl)-3-O-(D-2-propionyl-L-alanyl-D-isoglutamine)-D-glucose 2-acetamido-6-O-behenoyloxyacetyl-2-deoxy-3-O-(D-2-propionyl-L-alanyl-D-isoglutamine)-D-glucose 2-acetamido-6-O-[d-2-(3-chloro-4-cyclohexylphenyl)-propionyl]-2-deoxy-3-O-(D-2-propionyl-L-alanyl-D-isoglutamine)-D-glucose 2-acetamido-2-deoxy-6-O-(N-palmitoyl-L-prolyl)-3-O-(D-2-propionyl-L-alanyl-D-isoglutamine)-D-glucose 2-Acetamido-2-deoxy-6-O-(2-methyl-2-N-palmitoylamidopropionyl)-3-O-(D-2-propionyl-L-alanyl-D-isoglutamine)-D-glucose 2-acetamido-2-deoxy-6-O-(N-palmitoylglycyl)-3-O-(D-2-propionyl-L-alanyl-D-isoglutamine)-D-glucose 2-acetamido-2-deoxy-6-O-(N-palmitoyl-L-valyl)-3-O-(D-2-propionyl-L-alanyl-D-isoglutamine)-D-glucose 2-acetamido-2-deoxy-6-O-(N-palmitoyl-L-phenylalanyl)-3-O-(D-2-propionyl-L-alanyl-D-isoglutamine)-D-glucose 2-acetamido-2-deoxy-6-O-(N,O-dihexadecyl-D,L-seryl)-3-O-(D-2-propionyl-L-alanyl-D-isoglutamine)-D-glucose 2-acetamido-2-deoxy-6-O-(D,L-2-palmitamido-palmitoyl)-3-O-(D-2-propionyl-L-alanyl-D-isoglutamine)-D-glucose 2-acetamido-2-deoxy-6-O-(N,N'-dipalmitoyl-L-lysyl)-3-O-(D-2-propionyl-L-alanyl-D-isoglutamine)-D-glucose 2-acetamido-2-deoxy-6-O-(N-hexadecanesulfonylglycyl)-3-O-(D-2-propionyl-L-alanyl-D-isoglutamine)-D-glucose Bis(6-O-muramyl dipeptide)O-palmitoyltartronate 2-acetamido-6-O-cholesteryloxycarbonyl-2-deoxy-3-O-(D-2-propionyl-L-alanyl-D-isoglutamine)-D-glucose Methyl 2-acetamido-2-deoxy-6-O-hexadecyloxycarbonyl-3-O-(D-2-propionyl-L-alanyl-D-isoglutamine)-$\beta$-D-glucose Methyl 2-acetamido-6-O-behenoylisobutyryl-2-deoxy-3-O-(D-2-propionyl-L-alanyl-D-isoglutamine)-$\beta$-D-glucose 2-acetamido-2-deoxy-6-O-(16-hydroxyhexadecanoyl)-3-O-(D-2-propionyl-L-alanyl-D-isoglutamine)-D-glucose 2-acetamido-6-O-(16-acetoxyhexadecanoyl)-4-O-acetyl-3-O-(D-2-propionyl-L-alanyl-D-isoglutamine)-D-glucose 2-acetamido-2-deoxy-6-O-(2-furoyl)-3-O-(D-2-propionyl-L-alanyl-D-isoglutamine)-D-glucose 2-acetamido-2-deoxy-4,6-di-O-methoxyacetyl-3-O-(D-2-propionyl-L-alanyl-D-isoglutamine)-D-glucose 2-acetamido-4,6-di-O-acetamidoacetyl-2-deoxy-3-O-(D-2-propionyl-L-alanyl-D-isoglutamine)-D-glucose 2-acetamido-2-deoxy-6-O-(5-ketohexanoyl)-3-O-(D-2-propionyl-L-alanyl-D-isoglutamine)-D-glucose 2-acetamido-6-O-(6-aminohexanoyl)-2-deoxy-3-O-(D-2-propionyl-L-alanyl-D-isoglutamine)-D-glucose 2-acetamido-6-O-(6-acetamidohexanoyl)-2-deoxy-3-O-(D-2-propionyl-L-alanyl-D-isoglutamine)-D-glucose 2-acetamido-2-deoxy-6-O-(phenylacetyl)-3-O-(D-2-propionyl-L-alanyl-D-isoglutamine)-D-glucose 2-acetamido-2-deoxy-6-O-(phenoxyacetyl)-3-O-(D-2-propionyl-L-alanyl-D-isoglutamine)-D-glucose 2-acetamido-2-deoxy-6-O-(ethoxycarbonyl)-3-O-(D-2-propionyl-L-alanyl-D-isoglutamine)-D-glucose 2-acetamido-2-deoxy-6-O-(1-tetrazolylacetyl)-3-O-(D-2-propionyl-L-alanyl-D-isoglutamine)-D-glucose The Formula I compounds can be used in the form of salts derived from inorganic or organic acids. Included among such salts are the following: acetate, adipate alginate, aspartate, benzoate, benzenesulfonate, bisulfate, butyrate, citrate, camphorate, camphorsulfonate, cyclopentanepropionate, digluconate, dodecylsulfate, ethanesulfonate, fumarate, glucoheptanoate, glycerophosphate, hemisulfate, heptanoate, hexanoate, hydrochloride, hydrobromide, hydroiodide, 2-hydroxyethanesulfonate, lactate, maleate, methanesulfonate, 2-naphthalenesulfonate, nicotinate, oxalate, pamoate, pectinate, persulfate, succinate, tartrate, thiocyanate, tosylate, and undecanoate. Also, the basic nitrogen-containing groups can be quaternized with such agents as lower alkyl halides, such as methyl, ethyl, propyl, and butyl chloride, bromides and iodides; dialkyl sulfates like dimethyl, diethyl, dibutyl, and diamyl sulfates; long chain halides such as decyl, lauryl, myristyl and stearyl chlorides, bromides and iodides, aralkyl halides like benzyl and phenethyl bromides and others. Water or oil-soluble or dispersible products are thereby obtained.

The compounds in the present invention possess immunostimulatory properties and may be used as immunological adjuvants to stimulate the host immune response. They are especially useful for increasing the antigenicity of weakly immunogenic agents in vaccines against bacterial, viral, or parasitic infections or against various tissue antigens of normal or pathogenic origin. They can be used in place of whole killed mycobacterial cells in Freund's Complete Adjuvant. In addition, the compounds of the present invention when incorporated into a vaccine either as an aqueous or oil formulation lack the deleterious side effects observed in vaccine compositions containing Freund's Complete Adjuvant. Furthermore, the compounds of the present invention by themselves provide non-specific, host protection against infectious organisms, for example, *Klebsiella pneumoniae, Candida albicans* or *Staphylococcus aureus* and may be employed for this purpose in an antibacterial composition with a physiologically acceptable medium.

Intermediates for the compounds of Formula I may be prepared by condensing, using conventional procedures, a protected compound of Formula II with a protected compound of Formula III.

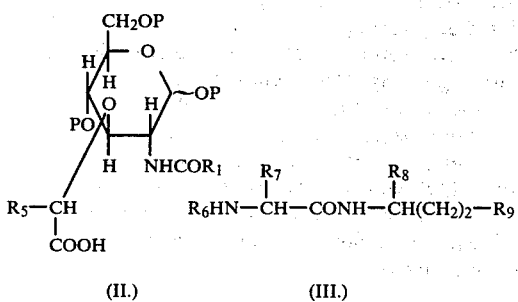

(II.)                (III.)

In the foregoing formulas, $R_1$, $R_5$, $R_6$, $R_7$, $R_8$ and $R_9$ represent the groups mentioned previously while P is a protecting group. The protecting group may be any suitable to protect the group to which it is attached during the condensation reaction and which may be readily removed thereafter. As protecting groups for the carboxyl group, there may be mentioned tertiary-butyl, benzyl or benzhydryl. For the hydroxyl groups, there may be mentioned the acyl radical, for example, the alkanoyl radical, such as acetyl, the aroyl radical, such as benzoyl, and, in particular, radicals derived from carbonic acid, such as benzyloxycarbonyl or lower alkyloxycarbonyl. Also to be mentioned are alkyl radicals, such as tertiary-butyl, benzyl, nitrobenzyl, lower alkoxy radical, or the tetrahydropyranyl radical. In addition, there may be mentioned the optionally substituted alkylidene radicals that block the oxygen atoms at the C-4 and C-6 positions. Among the alkylidene radicals, one finds, in particular, the lower alkylidene radicals, especially ethylidene, isopropylidene, or propylidene, and also, the optionally substituted benzylidene radical, preferentially substituted at the para position. For a more complete listing of protecting groups, reference may be had to standard works on peptide chemistry, e.g. Bodanszky et al., *Peptide Synthesis*, Chapter 4, Interscience Publishers, (1966), or Schroeder et al., *The Peptides* Vol. I, pp. xxiii–xxix, Academic Press, (1965), and to the text *Protective Groups in Organic chemistry*, Plenum Press, (1973), J. F. W. McOmie, (ed.).

The condensation is effected by reacting the compound II in the form where the carboxylic acid is activated with the amino compound III. The activated carboxyl group may be, for example, an acid anhydride, preferably, a mixed acid anhydride like an acetate of the acid, an amide of the acid like an imidazolid, an isoxazolid or an activated ester. The activated esters, include the cyanomethyl ester, the carboxylmethyl ester, the p-nitrophenyl thioester, the p-nitrophenyl ester, the 2,4,5-trichlorophenyl ester, the pentachlorophenyl ester, the N-hydroxysuccinimide ester, the N-hydroxyphthalimide ester, the 8-hydroxy-quinoline ester, the 2-hydroxy-1,2-dihydro-1-carboethoxyquinoline esters, the N-hydroxypiperidine ester or enol ester derived from N-ethyl-5-phenyl-isoxazolium-3'-sulfonate. The activated esters may equally be obtained from a carbodiimide by addition of N-hydroxysuccinimide or from a substituted 1-hydroxybenzyltriazole for example, a halogen, methyl, or methoxy-substituted 3-hydroxy-4oxo-3,4-dihydrobenzo[d]-1,2,3-triazine.

The amino group may be activated, for example, by reaction with a phosphitamide.

Among the methods of reaction with the activated esters, one must mention in particular those that involve N-ethyl-5-phenyl-isoxazolium-3'-sulfonate (Woodward's Reagent K), N-ethoxy-carbonyl-2-ethoxy-1,2-dihydroquinoline, or carbodiimide. Upon completion of the coupling reaction, the protecting groups may be removed in conventional manner to yield a compound from which a compound of Formula I may be prepared.

The starting materials utilized are known or can be made in a known fashion. Thus, one can obtain compounds of Formula II, for example, by reacting the corresponding sugar unsubstituted at position-3 with a halogen-$R_5$-acetic acid where $R_5$ has the meaning mentioned above. The ether is obtained in the presence of a strong base. The halogen is preferentially bromo or chloro.

Another process of synthesizing intermediates for the compounds of Formula I consists of condensation and eventual deblocking in conventional manner of the protecting groups present in a compound of Formula IV.

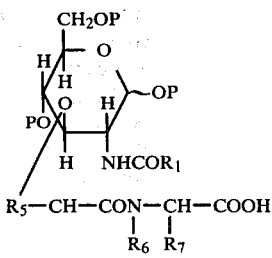

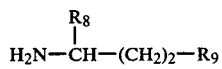

wherein $R_1$, $R_5$, $R_6$, and $R_7$ and P have the meaning mentioned above, with a compound of Formula V.

$$H_2N-\underset{\underset{R_8}{|}}{CH}-(CH_2)_2-R_9 \qquad (V.)$$

wherein $R_8$ and $R_9$ have the meaning mentioned above.

The condensation may be effected by reacting compound IV in the form of an activated carboxylic acid with the amino compound V or by reacting IV in the form of the free C-terminal carboxyl group with compound V where the amino group is present in activated form. The activated carboxyl group can be, for example, an acid anhydride and preferably a mixed acid anhydride, an acid amide or an activated ester. Among these, one finds in particular the acid anhydrides, the amides, or the esters mentioned above. The amino groups may be activated, for example, by reaction with a phosphitamide. The readily removable protecting groups correspond to those mentioned above.

The starting materials are obtained in classical fashion. One can, therefore,, react the corresponding sugar unsubstituted at position-3 with halogen-$R_5$-acetamido-$R_7$-acetic acid or a compound of Formula II with an amino-$R_7$-acetic acid where the carboxyl group is blocked as mentioned above followed by removal of the protecting groups.

Another process for inserting the side chain at position-3 of the sugar radical consists in reacting a compound having structure VI

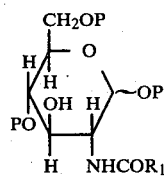

where $R_1$ and P have the signification mentioned above with a compound of Formula VII

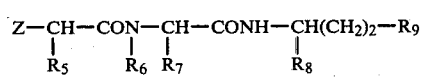

where Z represents an esterified hydroxy group capable of reacting and wherein $R_5$, $R_6$, $R_7$, $R_8$ and $R_9$ have the meaning given above followed by removal of the protecting groups optionally present. An esterified hydroxy group capable of reacting is, first of all, a hydroxy group esterified with a strong inorganic or organic acid and especially a group esterified by the hydrohalic acids, like hydrochloric acid, hydrobromic acid, or hydroiodic acid. The protecting groups correspond to those already mentioned above. One can re-move them in a classical fashion, for example, by hydrogenolysis with hydrogen in the presence of a noble metal catalyst, such as palladium or platinum, or by acid hydrolysis. The starting materials utilized in this preparative route are known.

One can also obtain the intermediates for the compounds of Formula I by acid hydrolysis of the oxazoline and dioxalane rings in the compound of Formula VIII,

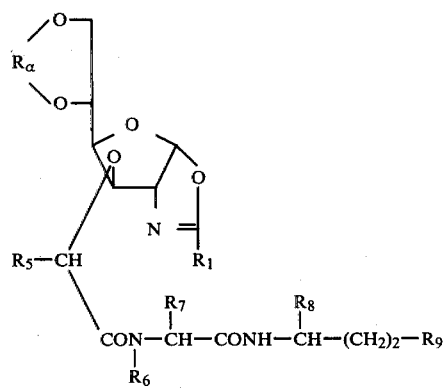

where $R_1$, $R_5$, $R_6$, $R_7$, $R_8$ and $R_9$ have the meaning mentioned above and where $R_\alpha$ is an alkylidene or cycloalkylidene group, and by removing the protecting groups optionally present.

Alkylidene signifies, particularly in this case, a lower alkylidene, such as isopropylidene and cycloalkylidene, especially cyclopentylidene or cyclohexylidene. This hydrolysis is effected equally in a classical fashion, for example, with acidic ion exchange resins, in particular, with an exchange-resin containing sulfonic acid groups like Amberlite IR-120, (resins of styrene containing stongly acidic sulfonyl groups) or Dowex-50 (polystyrene sulfonic acids) or with a strong inorganic or organic acid like hydrochloric acid, hydrobromic acid, sulfuric acid or a sulfonic acid like methanesulfonic acid or a phenylsulfonic acid optionally substituted in its aromatic nucleus, like p-toluenesulfonic acid, or trifluoroacetic acid.

In the presence of water, one obtains at position-1 a free hydroxy group. In the presence of an alcohol of formula $R_2OH$, where $R_2$ represents an optionally substituted alkyl group, one obtains the corresponding $R_2$ substituted compound. If one of the $R_8$ or $R_9$ carboxyl protecting groups P is the moiety resulting from esterifying the carboxyl group with an alcohol, in particular by a lower alcohol, the alcohol may be hydrolyzed, particularly at high temperature, with aqueous acid to liberate the free acid. During this hydrolysis it is possible that the amino group at position-2 of the molecule of the sugar may be liberated. One must in this case lastly insert the group

This is achieved in the usual fashion by acylation. In the resulting compounds, the protecting groups may be removed from the peptide radical, for example, by hydrogenolysis, such as with activated hydrogen in a catalytic fashion, or by hydrolysis. The starting materials utilized here are obtained, for example, by inserting the radical $R_5$-acetamidopeptide in one or several steps in the corresponding oxazoline with a free hydroxy group at position-3 of the sugar radical.

Compounds wherein $R_7$ is other than methyl, may be obtained when, for example, one of the following amino acids is substituted for alanine:

| Amino acid | $R_7$ |
|---|---|
| serine | $CH_2OH$ |
| cysteine | $CH_2SH$ |
| phenylalanine | benzyl |
| tyrosine | p-hydroxybenzyl |
| valine | isopropyl |
| leucine | 2-methylpropyl |
| isoleucine | 1-methylpropyl |
| α-aminobutyric | $CH_2CH_3$ |
| norvaline | $CH_2CH_2CH_3$ |
| norleucine | $CH_2CH_2CH_2CH_3$ |

Compounds wherein $R_6$ and $R_7$ together are $-CH_2CH_2CH_2-$ are obtained by substituting proline for alanine.

The term "substituted alkyl" for $R_1$ and $R_2$ refers to an alkyl group of from 1 to 7 carbon atoms substituted by hydroxy, mercapto, alkoxy of 1-3 carbons, alkyl mercapto of 1-3 carbons, hydroxy or mercapto esterified by an acid of 1-4 carbon atoms, halogen (F, Cl or Br), carboxyl, or carboxyl functionally modified by esterification with a lower alcohol of 1-3 carbons or by amidation. Preferably the alkyl substituents are hydroxy or mercapto, either free or substituted by an alkyl group of 1-3 carbons.

The substituents in the terms "substituted phenyl" for $R_1$ and $R_2$ or "substituted phenyl $C_{1-4}$ alkyl" for $R_2$ refer to the phenyl group substituted by one or more alkyl groups of 1-3 carbon atoms or hydroxy or mercapto groups either free, or etherified by an alkyl group of 1-3 carbons or esterified by an acid of 1-4 carbons, lower (1-4C) alkyldioxy, cycloalkyldioxy of 5-7 carbon atoms, amino, or trifluoromethyl.

The substituents in the term "substituted phenyl" for $R_{10}$, are halo and phenyl.

Compounds wherein $R_2$ is hydrogen and $R_1$ is other than methyl are obtained by reacting 2-amino-2-deoxy-D-glucose, in the case where $R_1$ is alkyl or substituted-alkyl, with the appropriate alkanoic anhydride or alkanoyl halide, preferably chloride, or substituted-alkanoic anhydride or substituted-alkanoyl halide, preferably chorlide, and in the case where $R_1$ is phenyl or substituted-phenyl, with the appropriate aroic anhydride or aroyl halide, preferably chloride, or substituted aroic anhydride or substituted aroyl halide, preferably chloride, in the presence of an appropriate acid acceptor, such as pyridine or triethylamine. The protecting groups P are then introduced at the C-1, C-4, and C-6 positions to give a compound of Formula VI which may then be converted to a compound of Formula II or Formula IV.

In general, compounds wherein $R_2$ is other than hydrogen are prepared by reacting an alcohol of formula $R_2OH$ with the N-alkanoylglucosamine or N-aroylglucosamine to give the corresponding alkyl, substituted alkyl, phenyl, substituted phenyl, phenyl $C_{1-4}$ alkyl, or substituted phenyl $C_{1-4}$ alkyl glucopyranoside. The latter are then treated to block the C-4 and C-6 hydroxyl groups, for example, as benzylidene acetal, by reaction with benzyladehyde and boron trifluoride etherate or zinc chloride. The blocked $R_5$-acetamidodipeptide fragment is then inserted into the blocked glucopyranoside having a free hydroxyl group at position -3 of the sugar radical in one or several steps as described above. The protecting groups are then removed by hydrogenolysis with hydrogen in the presence of a noble metal catalyst, or by acid hydrolysis.

For $R_8$ and $R_9$, among the optionally esterified carboxyl groups can be mentioned the carboxyl group esterified by a lower alcohol of 1-3 carbons, like methanol or ethanol. The carboxyl group can also be amidated, unsubstituted at the nitrogen atom or mono- or di-substituted with an alkyl, in particular, a lower alkyl, an aryl, particularly phenyl, or an aralkyl, particularly benzyl.

Most preferably, $R_2$ is H, alkyl of 1-3 carbons, benzyl, phenyl or phenyl p-substituted by alkyl (1-3C), amino, halogen, hydroxy or trifluoromethyl; $R_1$ is alkyl of 1-3 carbons, or phenyl, or phenyl p-substituted by alkyl (1-3C), amino, halogen, hydroxy or trifluoromethyl, $R_5$ is H or lower alkyl of 1-3 carbons; $R_7$ is H, alkyl of 1-4 carbons, hydroxymethyl, mercaptomethyl, benzyl or p-hyroxybenzyl; $R_6$ and $R_7$ together are $-CH_2CH_2CH_2-$; and $R_8$ and $R_9$ are carboxyl, carboxyl esterified by an alcohol of 1-4 carbons, carboxamide, or monoalkyl or dialkyl substituted carboxamide wherein the alkyl group has from 1-3 carbons.

The compounds of Formula I are prepared by reaction of the intermediates described above with the appropriate acid whereby condensation results in the desired 6—O— and/or 4—O— substituted compounds. All of the appropriate acids for preparing the compounds of Formula I are known compounds or may be prepared by known methods in an obvious manner. The condensation reaction will take place preferentially at the 6-position of the glucose ring, thus giving predominantly or exclusively 6—O— derivatives under normal reaction conditions. When the reaction conditions are driven, 4—O— derivatives can also be obtained, giving 6—O— and 4—O— derivatives. Where it is desired to prepare only 4—O— derivatives, the 6-position must be blocked while the 4-position substitution takes place, followed by deblocking. The blocking and deblocking reactions may be carried out in accordance with procedures well-known in the art.

The condensation reactions may be carried out in accordance with procedures well established in the art for preparing organic compounds. Thus, the condensation may be carried out using the carboxylic acid, the acid anhydride, or the acid halide.

Where the carboxylic acid is utilized, a coupling agent, for example N,N-dicyclohexylcarbodiimide (DCC), or 4-dimethylaminopyridine (DMAP), will be employed. The reaction is carried out in an inert aprotic solvent, such as dimethylformamide, dimethylsulfoxide, or pyridine, at a temperature of from 0° to 50° C. for from 6 hours to 6 days.

Where the acid anhydride is utilized, a coupling agent may be employed, although this is not necessary. However, an acid acceptor, such as pyridine or trimethylamine, should be used. The solvent medium in which the reaction is carried out and the other reaction conditions are the same as for the carboxylic acid condensation.

Where the acid halide is utilized, all of the reaction conditions are the same as those for the acid anhydride condensation.

Once the condensation reaction has been completed, the remaining protecting groups are readily removed by hydrogenolysis, preferably carried out with a catalyst such as palladium oxide in the presence of glacial acetic acid.

The obtained compounds can be transformed to their salts in a classical fashion, for example, by reacting the acidic compounds obtained, with alkaline or alkaline earth hydroxides or the basic compounds with acids.

The present invention is also directed to pharmaceutical preparations that contain a compound of Formula I. Among the pharmaceutical preparations relevant to this invention are salts that are administered by external route, for example, orally, rectally or parenterally to mammalian species. Preparations may be administered that contain the pharmacologically active compound by itself or mixed with a pharmaceutically acceptable carrier. The dose of the pharmacologically active compound depends on the animal specie, the age, and the state of the individual and the mode of application.

The new pharmaceutical preparations contain from about 10% to about 95% and, preferably from about 20% to about 90% of a compound of the present invention. The pharmaceutical preparation relevant to this invention can be presented, for example, in the form of unit doses like tablets, capsules, suppositories, and ampoules.

The immunostimulatory properties of the compounds in the present invention can be demonstrated with the following protocols:

1. In vivo Stimulation of Humoral Response: Increase in the Production of Antibodies Against Bovine Serum Albumin (BSA) in the Mouse Mice (NMRI) are immunized by i.p. injections of 10 mg of BSA without precipitate. At 0, 9, 15 and 29 days later blood samples are taken and analyzed for anti-BSA-antibody titers by the passive hemagglutination technique. At the dose utilized, soluble BSA is subimmunogenic for the receiving animals, that is, it does not cause any antibody production, or at most a completely insignificant production. Additional treatment of the mice with certain immunostimulants before or after administration of antigen leads to an increase in antibody titer in the serum. The effect of the treatment is expressed by the obtained score, that is, the sum of the logs to the base 2 of the differences of the titer at 3 days of bleeding.

The compounds of the present invention are capable of augmenting in a significant manner the production of anti-BSA antibodies by i.p. or subcutaneous application (s.c.) of 100–300 mg/kg/animal during 5 consecutive days (day 0 to day 4) after immunization with BSA.

The immunostimulatory effect of the compounds mentioned herein depend on the antigen, contrary to other bacterial immunostimulants (like LPS of *E. coli*). The injection of the compounds of the present invention results in augmentation of anti-BSA antibody titer only in mice immunized with BSA, and not with non-immunized mice. Subcutaneous administration is as efficacious as i.p., that is, the immunostimulatory effect observed is systemic and does not depend on the fact that the stimulant was administered by the same route as the antigen or mixed with it, as is the case with classical adjuvants.

The compounds of the present invention permit specific augmentation of humoral immunity, improve immune response, and provide long-lasting immunostimulatory effects on systemic activation of immune apparatus.

2. Stimulation of Mitotic Responses of Lymphocyte Cultures

Mouse lymphoid cells are cultured in microtiter plates, in RPMI-1640 medium with 2% fetal calf serum. Cultures are set in triplicates and consist of $3-5 \times 10^5$ spleen or $1.5 \times 10^6$ thymus cells per well in a final volume of 0.2 ml. Class specific mitogens are added at optimal or suboptimal concentrations, while control cultures are incubated without mitogens. The tested compounds are added shortly after the mitogens and the cultures are incubated for 48 hours at 37° with 5% $CO_2$. Incorporation of tritiated thymidine is determined after a pulse (1.0 $\mu$Ci/well) during the last 6 hours in culture. The data are recorded as mean cpm and the effects of the compounds are presented as stimulation index (mean cpm in cultures with the compound/mean cpm in control).

The compounds of the present invention enhance the levels of thymidine incorporation in lymphocyte cultures, with or without mitogens. The stimulation indices are maximal in control cultures or in those with suboptimal doses of mitogens. Similar effects of the compound are provoked in cultures of different lymphocyte populations, namely, B cells (nude spleen), T cells (thymus) or their mixtures (normal spleen). The effects of the compounds are dose-dependent. These compounds, therefore, are capable of stimulating proliferation of lymphocytes that participate in the humoral response (B cells) as well as in cellular immunity (T cells).

3. Compatibility

Although the compounds of the present invention produce their stimulatory effect with guinea pigs, for example, beginning with a single dose of 0.05 mg/kg s.c., and with mice after 5 applications of 10 mg/kg s.c., no toxic effect is observed after 5 applications of 300 mg/kg i.p., with the mouse. These compounds possess, therefore, a remarkable therapeutic index.

The compounds of the present invention thus have the capacity, on the one hand, of being mixed with an antigen for which an increase in immunogenicity is required and on the other hand, by systemic application, of increasing the immunological reactivity of the treated organism. Moreover, these compounds can enhance cellular as well as humoral immunity and activate lymphocytes responsible for the formation of antibodies.

The compounds of the present invention can consequently be employed as (1) adjuvants by mixing them with vaccines with the goal of improving the effectiveness of the vaccination and (2) protective agents against infections caused by bacteria, viruses or pathogenic parasites, owing to immunity by humoral antibodies and/or to cellular mediation.

Thus, the described compounds are indicated, mixed with the most varied antigens, as adjuvants for experimental as well as industrial production of antisera for therapeutic and diagnostic purposes, as well as to induce immunologically active lymphocyte populations at the time of cell transfers.

Moreover, one can equally utilize the new compounds without simultaneously supplying antigen in order to enhance immune reactions that are already taking place in a subliminal fashion in a mammalian host. These compounds are therefore especially indicated for stimulation of individual immune defense, e.g., at the time of chronic or acute infections or in cases of selective (antigen-specific) immunological deficiencies as well as in situations of immune deficiency, but also acquired general deficiency (i.e., not antigen-specific) as appears with age, during intial shock from a grave illness, and before and soon after radiation therapy or immunosuppressive hormones. The said compounds can subsequently be administered in combination with antiinfectious antibiotics, chemical therapeutics or other methods of treatment, to combat immunological deficiencies. The described compounds are thus indicated equally for general prophylaxis of infectious disease in man and animal.

EXAMPLE 1

Preparation of 2-acetamido-6-O-behenoyloxyisobutyryl-2-deoxy-3-O-(D-2-propionyl-L-alanyl-D-isoglutamine)-D-glucose Step A: Preparation of benzyl-2-acetamido-6-O-behenoyloxyisobutyryl-2-deoxy-3-O-D-2-propionyl-L-alanyl-(D-isoglutamine benzyl ester)-α-D-glucopyranoside To benzyl 2-acetamido-2-deoxy-3-O-(D-2-propionyl-L-alanyl-D-isoglutamine benzyl ester)-α-D-glucopyranoside (0,447 mmol) was added dimethylformamide (4 ml.), behenoyloxyisobutyric acid (0.50 mmol), then dichloromethane (6 ml.), N,N'-dicyclohexylcarbodiimide (0.50 mmol) and 4-dimethylaminopyridine (0.50 mmol). The mixture was stirred for 4 days at room temperature. The mixture was added to dichloromethane, washed with water and the product purified by preparative thin layer chromatography (silica) using chloroform/methanol/water: 85/15/1.5.

Step B: Preparation of 2-acetamido-6-O-behenoyloxyisobutyryl-2-deoxy-3-O-(D-2-propionyl-L-alanyl-D-isoglutamine)-D-glucose To benzyl 2-acetamido-6-O-behenoyloxyisobutyryl-2-deoxy-3-O-(D-2-propionyl-L-alanyl-D-isoglutamine benzyl ester)-α-D-glucopyranoside (0.218 mmol) was added acetic acid (5 ml.) and palladium oxide (210 mg.). This mixture was shaken in a hydrogen atmosphere for 2 days. The solvent was removed in vacuo and the product purified by preparative thin layer chromatography (silica) using chloroform/methanol/water: 80/20/2.

EXAMPLE 2

Preparation of 2-acetamido-2-deoxy-6-O-(N,O-dipalmitoyl-D,L-seryl)-3-O-(D-2-propionyl-L-alanyl-D-isoglutamine)-D-glucose Employing the procedure substantially as described in Example 1, but substituting for the behenoyloxyisobutyric acid used in Step A thereof, an equivalent amount of N,O-dipalmitoyl-D,L-serine, there are prepared in sequence,
Step A: Benzyl 2-acetamido-2-deoxy-6-O-(N,O-dipalmitoyl-D,L-seryl)-3-O-(D-2-propionyl-L-alanyl-D-isoglutamine benzyl ester)-α-D-glucopyranoside
Step B: 2-Acetamido-2-deoxy-6-O-(N,O-dipalmitoyl-D,L-seryl)-3-O-(D-2-propionyl-L-alanyl-D-isoglutamine)-D-glucose

EXAMPLE 3

Preparation of 2-acetamido-6-O-(adamantane-1-carbonyl)-3-O-(D-2-propionyl-L-alanyl-D-isoglutamine)-D-glucose Employing the procedure substantially as described in Example 1, but substituting for the behenoyloxyisobutyric acid used in Step A thereof, an equivalent amount of adamantane-1-carboxylic acid, there are prepared in sequence,
Step A: Benzyl 2-acetamido-2-deoxy-6-O-(adamantane-1-carbonyl)-3-O-(D-2-propionyl-L-alanyl-D-isoglutamine benzyl ester)-α-D-glucopyranoside
Step B: 2-Acetamido-2-deoxy-6-O-(adamantane-1-carbonyl)-3-O-(D-2-propionyl-L-alanyl-D-isoglutamine)-D-glucose

EXAMPLE 4

Preparation of 2-Acetamido-6-O-behenoyloxyacetyl-2-deoxy-3-O-(D-2-propionyl-L-alanyl-D-isoglutamine)-D-glucose Employing the procedure substantially as described in Example 1, but substituting for the behenoyloxyisobutyric acid used in Step A thereof, an equivalent amount of behenoyloxyacetic acid, there are prepared in sequence,
Step A: Benzyl 2-acetamido-6-O-behenoyloxyacetyl-2-deoxy-3-O-(D-2-propionyl-L-alanyl-D-isoglutamine benzyl ester)-α-D-glucopyranoside
Step B: 2-Acetamido-6-O-behenoyloxyacetyl-2-deoxy-3-O-(D-2-propionyl-L-alanyl-D-isoglutamine)-D-glucose

EXAMPLE 5

Preparation of 2-Acetamido-6-O-[d-2-(3-chloro-4-cyclohexylphenyl)-propionyl]-2-deoxy-3-O-(D-2-propionyl-L-alanyl-D-isoglutamine)-D-glucose Employing the procedure substantially as described in Example 1, but substituting for the behenoyloxyisobutyric acid used in Step A thereof, an equivalent amount of d-2-(3-chloro-4-cyclohexylphenyl)propionic acid, there are prepared in sequence,
Step A: Benzyl 2-acetamido-2-deoxy-6-O-[d-2-(3-chloro-4-cyclohexylphenyl)propionyl]-2-deoxy-3-O-(D-2-propionyl-L-alanyl-D-isoglutamine benzyl ester)-α-D-glucopyranoside
Step B: 2-Acetamido-2-deoxy-6-O-[d-2-(3-chloro-4-cyclohexylphenyl)propionyl]-2-deoxy-3-O-(D-2-propionyl-L-alanyl-D-isoglutamine)-D-glucose

EXAMPLE 6

Preparation of 2-Acetamido-2-deoxy-6-O-(N-palmitoyl-L-prolyl)-3-O-(D-2-propionyl-L-alanyl-D-isoglutamine)-D-glucose Employing the procedure substantially as described in Example 1, but substituting for the behenoyloxyisobutyric acid used in Step A thereof, an equivalent amount of N-palmitoyl-L-proline, there are prepared in sequence,
Step A: Benzyl 2-acetamido-2-deoxy-6-O-(N-palmitoyl-L-prolyl)-3-O-(D-2-propionyl-L-alanyl-D-isoglutamine benzyl ster)-α-D-glucopyranoside
Step B: 2-Acetamido-2-deoxy-6-O-(N-palmitoyl-L-prolyl)-3-O-(D-2-propionyl-L-alanyl-D-isoglutamine)-D-glucose

EXAMPLE 7

Preparation of
2-Acetamido-2-deoxy-6-O-(2-methyl-2-N-palmitoylamidopropionyl)-3-O-(D-2-propionyl-L-alanyl-D-isoglutamine)-D-glucose Employing the procedure substantially as described in Example 1, but substituting for the behenoyloxyisobutyric acid used in Step A thereof, an equivalent amount of 2-methyl-2-N-palmitoylamidopropionic acid, there are prepared in sequence, Step A: Benzyl 2-acetamido-2-deoxy-6-O-(2-methyl-2-N-palmitoylamidopropionyl)-3-O-(D-2-propionyl-L-glucopyranoside Step B: 2-Acetamido-2-deoxy-6-O-(2-methyl-2-N-palmitoylamidopropionyl)-3-O-(D-2-propionyl-L-alanyl-D-isoglutamine)-D-glucose

EXAMPLE 8

Preparation of
2-acetamido-2-deoxy-6-O-(N-palmitoylglycyl)-3-O-(D-2-propionyl-L-alanyl-D-isoglutamine)-D-glucose Employing the procedure substantially as described in Example 1, but substituting for the behenoyloxyisobutyric acid used in Step A thereof, an equivalent amount of N-palmitoylglycine, there are prepared in sequence, Step A: Benzyl 2-acetamido-2-deoxy-6-O-(N-palmitoylglycyl)-3-O-(D-2-propionyl-L-alanyl-D-isoglutamine benzyl ester)-α-D-glucopyranoside Step B: 2-Acetamido-2-deoxy-6-O-(N-palmitoylglyclyl)-3-O-(D-2-propionyl-L-alanyl-D-isoglutamine)-D-glucose

EXAMPLE 9

Preparation of
2-acetamido-2-deoxy-6-O-(N-palmitoyl-L-valyl)-3-O-(D-2-propionyl-L-alanyl-D-isoglutamine)-D-glucose Employing the procedure substantially as described in Example 1, but substituting for the behenoyloxyisobutyric acid used in Step A thereof, an equivalent amount of N-palmitoyl-L-valine, there are prepared in sequence, Step A: Benzyl 2-acetamido-2-deoxy-6-O-(N-palmitoyl-L-valyl)-3-O-(D-2-propionyl-L-alanyl-D-isoglutamine benzyl ester)-α-D-glucopyranoside Step B: 2-Acetamido-2-deoxy-6-O-(N-palmitoyl-L-valyl)-3-O-(D-2-propionyl-L-alanyl-D-isoglutamine)-D-glucose

EXAMPLE 10

Preparation of
2-acetamido-2-deoxy-6-O-(N-palmitoyl-L-phenylalanyl)-3-O-(D-2-propionyl-L-alanyl-D-isoglutamine)-D-glucose Employing the procedure substantially as described in Example 1, but substituting for the behenoyloxyisobutyric acid used in Step A thereof, an equivalent amount of N-palmitoyl-L-phenylalanine, there are prepared in sequence, Step A: Benzyl 2-acetamido-2-deoxy-6-O-(N-palmitoyl-L-phenylalanyl)-3-O-(D-2-propionyl-L-alanyl-D-isoglutamine benzyl ester)-α-D-glucopyranoside Step B: 2-Acetamido-2-deoxy-6-O-(N-palmitoyl-L-phenylalanyl)-3-O-(D-2-propionyl-L-alanyl-D-isoglutamine)-D-glucose

EXAMPLE 11

Preparation of
2-acetamido-2-deoxy-6-O-(N,O-dihexadecyl-D,L-seryl)-3-O-(D-2-propionyl-L-alanyl-D-isoglutamine)-D-glucose Employing the procedure substantially as described in Example 1, but substituting for the behenoyloxyisobutyric acid used in Step A thereof, an equivalent amount of N,O-dihexadecyl-D,L-serine, there are prepared in sequence, Step A: Benzyl 2-acetamido-2-deoxy-6-O-(N,O-dihexadecyl-D,L-seryl)-3-O-(D-2-propionyl-L-alanyl-D-isoglutamine benzyl ester)-α-D-glucopyranoside Step B: 2-Acetamido-2-deoxy-6-O-(N,O-dihexadecyl-D,L-seryl)-3-O-(D-2-propionyl-L-alanyl-D-isoglutamine)-D-glucose

EXAMPLE 12

Preparation of
2-acetamido-2-deoxy-6-O-(D,L-2-palmitamidopalmitoyl)-3-O-(D-2-propionyl-L-alanyl-D-isoglutamine)-D-glucose Employing the procedure substantially as described in Example 1, but substituting for the behenoyloxyisobutyric acid used in Step A thereof, an equivalent amount of D,L-2-palmitamidopalmitic acid, there are prepared in sequence, Step A: Benzyl 2-acetamido-2-deoxy-6-O-(D,L-2-palmitamidopalmitoyl)-3-O-(D-2-propionyl-L-alanyl-D-isoglutamine benzyl ester)-α-D-glucopyranoside Step B: 2-Acetamido-2-deoxy-6-O-(D,L-2-palmitamidopalmitoyl)-3-O-(D-2-propionyl-L-alanyl-D-isoglutamine)-D-glucose

EXAMPLE 13

Preparation of
2-acetamido-2-deoxy-6-O-(N,N'-dipalmitoyl-L-lysyl)-3-O-(D-2-propionyl-L-alanyl-D-isoglutamine)-D-glucose Employing the procedure substantially as described in Example 1, but substituting for the behenoyloxyisobutyric acid used in Step A thereof an equivalent amount of N,N'-dipalmitoyl-L-lysine, there are prepared in sequence, Step A: Benzyl 2-acetamido-2-deoxy-6-O-(N,N'-dipalmitoyl-L-lysyl)-3-O-(D-2-propionyl-L-alanyl-D-isoglutamine benzyl ester)-α-D-glucopyranoside Step B: 2-Acetamido-2-deoxy-6-O-(N,N'-dipalmitoyl-L-lysyl)-3-O-(D-2-propionyl-L-alanyl-D-isoglutamine)-D-glucose

EXAMPLE 14

Preparation of bis (6-O-muramyl dipeptide) O-palmitoyltartronate

Employing the procedure substantially as described in Example 1, but substituting for the behenoyloxyisobutyric acid used in Step A thereof, half an equivalent amount of O-palmitoyltartronic acid, there are prepared in sequence, Step A: Bis(6-O-muramyl dipeptide α-benzylglycoside benzyl ester) O-palmitoyltartronate Step B: Bis(6-O-muramyl dipeptide) O-palmitoyltartronate

EXAMPLE 15

Preparation of
2-acetamido-6-O-cholesteryloxycarbonyl-2-deoxy-3-O-(D-2-propionyl-L-alanyl-D-isoglutamine)-D-glucose Step A: Preparation of 2-acetamido-6-O-cholesteryloxycarbonyl-2-deoxy-3-O-(D-2-propionyl-L-alanyl-D-isoglutamine benzyl ester)-α-D-glucopyranoside To benzyl 2-acetamido-2-deoxy-3-O-(D-2-propionyl-L-alanyl-D-isoglutamine benzyl ester)-α-D-glucopyranoside (0.149 mmol) was added dimethylformamide (1 ml.), then dry pyridine (0.62 mmol), then cholesteryl chloroformate (0.16 mmol) and dry dichloromethane (1 ml.). The mixture was stirred at room temperature. After 2 hours, more cholesteryl chloroformate (0.08 mmol) was added and after another hour again more cholesteryl chloroformate (0.16 mmol) was added. After two days at room temperature the mixture was added to dichloromethane (25 ml.) and dilute hydrochloric acid (50 ml.). The organic layer was separated, dried with magnesium sulfate, and the product purified by preparative thin layer chromatography on silica gel using chloroform/methanol/water: 90/10/1.

Step B: Preparation of 2-acetamido-6-O-cholesteryloxycarbonyl-2-deoxy-3-O-(D-2-propionyl-L-alanyl-D-isoglutamine)-D-glucose To benzyl 2-acetamido-6-O-cholesteryloxycarbonyl-2-deoxy-3-O-(D-2-propionyl-L-alanyl-D-isoglutamine benzyl ester)-α-D-glucopyranoside (0.096 mmol) was added acetic acid (5 ml.), and palladium oxide (100 mg.) and this mixture was shaken in a hydrogen atmosphere for two days. The catalyst was removed by filtration and the solvent evaporated to give the product.

EXAMPLE 16

Preparation of methyl
2-acetamido-2-deoxy-6-O-hexadecyloxycarbonyl-3-O-(D-2-propionyl-L-alanyl-D-isoglutamine)-β-D-glucopyranoside Step A: Preparation of methyl 2-acetamido-2-deoxy-6-O-hexadecyloxycarbonyl-3-O-(D-2-propionyl-L-alanyl-D-isoglutamine benzyl ester)-β-D-glucopyranoside To dry dichloromethane (3 ml.) was added phosgene in benzene (0.55 mmol), 1-hexadecanol (0.50 mmol) and pyridine (0.1 ml.). This mixture was then added to a stirred solution of methyl 2-acetamido-2-deoxy-3-O-(D-2-propionyl-L-alanyl-D-isoglutamine benzyl ester)-β-D-glucopyranoside (0.276 mmol) in dimethylformamide (3 ml.). After one day at room temperature the mixture was added to dichloromethane (25 ml.) and dilute hydrochloric acid (50 ml.). The organic phase was separated, dried with magnesium sulfate, and the product purified by preparative thin layer chromatography on silica gel using chloroform/methanol/water: 85/15/1.5.

Step B: Preparation of methyl 2-acetamido-2-deoxy-6-O-hexadecyloxycarbonyl-3-O-(D-2-propionyl-L-alanyl-D-isoglutamine)-β-D-glucopyranoside To methyl 2-acetamido-2-deoxy-6-O-hexadecyloxycarbonyl-3-O-(D-2-propionyl-L-alanyl-D-isoglutamine benzyl ester)-β-D-glucopyranoside (0.034 mmol) was added acetic acid (5 ml.), palladium oxide (100 mg.) and this mixture was shaken in a hydrogen atmosphere for 18 hours. The catalyst was removed by filtration and the solvent removed by evaporation to give the product.

EXAMPLE 17

Preparation of methyl
2-acetamido-6-O-behenoylisobutyryl-2-deoxy-3-O-(D-2-propionyl-L-alanyl-D-isoglutamine)-β-D-glucopyranoside Employing the procedure substantially as described in Example 1, but substituting for the benzyl 2-acetamido-2-deoxy-3-O-(D-2-propionyl-L-alanyl-D-isoglutamine benzyl ester)-α-D-glucopyranoside used in Step A thereof, an equivalent amount of methyl 2-acetamido-2-deoxy-3-O-(D-2-propionyl-L-alanyl-D-isoglutamine benzyl ester)-β-D-glucopyranoside, there are prepared in sequence, Step A: Methyl 2-acetamido-6-O-behenoylisobutyryl-2-deoxy-3-O-(D-2-propionyl-L-alanyl-D-isoglutamine benzyl ester)-β-D-glucopyranoside Step B: Methyl 2-acetamido-6-O-behenoylisobutyryl-2-deoxy-3-O-(D-2-propionyl-L-alanyl-D-isoglutamine)-β-D-glucopyranoside

EXAMPLE 18

Preparation of
2-acetamido-2-deoxy-6-O-(16-hydroxyhexadecanoyl)-3-O-(D-2-propionyl-L-alanyl-D-isoglutamine)-D-glucose Step A: Preparation of benzyl 2-acetamido-2-deoxy-6-O-(16-hydroxyhexadecanoyl)-3-O-(D-2-propionyl-L-alanyl-D-isoglutamine benzyl ester)-α-D-glucopyranoside To a stirred solution of 16-hydroxyhexadecanoic acid (135 mg., 0.50 mmol) in dry N,N-dimethylformamide (4 ml.) were added 4-dimethylaminopyridine (6 mg.) and benzyl 2-acetamido-2-deoxy-3-O-(D-2-propionyl-L-alanyl-D-isoglutamine benzyl ester)-α-D-glucopyranoside (300 mg., 0.45 mmol). The reaction mixture was cooled in an ice-bath, and N,N'-dicyclohexylcarbodiimide (DCC) (102 mg., 0.49 mmol) was added. After stirring for 5 hrs. at room temperature, additional 16-hydroxyhexadecanoic acid (135 mg.) and DCC (102 mg.) were added. The reaction mixture was then stirred overnight at room temperature. The precipitated solid was filtered, the filtrate evaporated, the residue taken up in chloroform, washed twice with 0.5 M hydrochloric acid and once with saturated aqueous sodium hydrogencarbonate. The organic layer was evaporated, the residue dissolved in the minimal volume of chloroform, the solution applied to a column of silica gel (Merck No. 7734) that was eluted with 20:1 chloroform-methanol. Evaporation of the appropriate fractions gave benzyl 2-acetamido-2-deoxy-6-O-(16-hydroxyhexadecanoyl)-3-O-(D-2-propionyl-L-alanyl-D-isoglutamine benzyl ester)-α-D-glucopyranoside as a chromatographically homogeneous solid, yield 103 mg. (25%).

The 300-MHz NMR spectrum in dimethylsulfoxide-$d_6$ was in accord with the desired structure.

Step B: Preparation of 2-acetamido-2-deoxy-6-O-(16-hydroxyhexadecanoyl)-3-O-(D-2-propionyl-L-alanyl-D-isoglutamine)-D-glucose A solution of benzyl 2-acetamido-2-deoxy-6-O-(16-hydroxyhexadecanoyl)-3-O-(D-2-propionyl-L-alanyl-D-isoglutamine benzyl ester)-α-D-glucopyranoside (93 mg.) in glacial acetic acid (3 ml.) was hydrogenolyzed for 48 hrs. at atmospheric pressure and room temperature in the presence of palladium (added as PdO, 150 mg.). The reaction mixture was filtered through Celite, the filtrate evaporated and coevaporated several times with toluene. The residue was dissolved in the minimal volume of chloroform-methanol (9:1) and the solution was applied to a column of silica gel (Merck No. 7734) that was eluted with initially 9:1 chloroform-methanol, then 80:20:2 chloroform-methanol-water, and finally with 70:30:3 chloroform-methanol-water. The fractions containing the desired product were combined and evaporated and the resulting solid coevaporated several times with diethyl ether and dried in vacuo over phosphorus pentoxide to afford pure 2-acetamido-2-deoxy-6-O-(16-hydroxyhexadecanoyl)-3-O-(D-2-propionyl-L-alanyl-D-isoglutamine)-D-glucose; yield 64 mg. (85%).

The 300-MHz NMR spectrum in dimethylsulfoxide -$d_6$ was in accord with the desired structure.

EXAMPLE 19

Preparation of 2-acetamido-6-O-(16-acetoxyhexadecanoyl)-4-O-acetyl-3-O-(D-2-propionyl-L-alanyl-D-isoglutamine)-D-glucose Step A: Preparation of benzyl 2-acetamido-6-O-(16-acetoxyhexadecanoyl)-4-O-acetyl-3-O-(D-2-propionyl-L-alanyl-D-isoglutamine benzyl ester)-α-D-glucopyranoside To a solution of benzyl 2-acetamido-2-deoxy-6-O-(16-hydroxyhexadecanoyl)-3-O-(D-2-propionyl-L-alanyl-D-isoglutamine benzyl ester)-α-D-glucopyranoside (103 mg.) in pyridine (1 ml.) was added acetic anhydride (0.5 ml.). The reaction mixture was stirred overnight at room temperature, evaporated, and coevaporated several times with toluene. The resulting solid was dried in vacuo to afford benzyl 2-acetamido-6-O-(16-acetoxyhexadecanoyl)-4-O-acetyl-2-deoxy-3-O-(D-2-propionyl-L-alanyl-D-isoglutamine benzyl ester)-α-D-glucopyranoside, yield 112 mg. (quantitative).

The 300-MHz NMR spectrum in dimethylsulfoxide-$d_6$ was in accord with the desired structure.

Step B: Preparation of 2-acetamido-6-O-(16-acetoxyhexadecanoyl)-4-O-acetyl-2-deoxy-3-O-(D-2-propionyl-L-alanyl-D-isoglutamine)-D-glucose A solution of benzyl 2-acetamido-6-O-(16-acetoxyhexadecanoyl)-4-O-acetyl-2-deoxy-3-O-(D-2-propionyl-L-alanyl-D-isoglutamine benzyl ester)-α-D-glucopyranoside (110 mg.) in glacial acetic acid (5 ml.) was hydrogenolyzed for 24 hrs. at atmospheric pressure and room temperature in the presence of palladium (added as PdO, 150 mg.). The reaction mixture was filtered through Celite, the filtrate evaporated, coevaporated several times with water and toluene. The resulting solid was dried in vacuo over phosphorus pentoxide to afford 2-acetamido-6-O-(16-acetoxyhexadecanoyl)-4-O-acetyl-2-deoxy-3-O-(D-2-propionyl-L-alanyl-D-isoglutamine)-D-glucose; yield 50 mg. (56%). The 300-NH$_Z$ NMR spectrum in dimethylsulfoxide -$d_6$ was in accord with the desired structure.

EXAMPLE 20

Preparation of 2-acetamido-2-deoxy-6-O-(2-furoyl)-3-O-(D-2-propionyl-L-alanyl-D-isoglutamine)-D-glucose Step A: Preparation of benzyl 2-acetamido-2-deoxy-6-O-(2-furoyl)-3-O-(D-2-propionyl-L-alanyl-D-isoglutamine benzylester)-α-D-glucopyranoside To a stirred solution of 2-furoic acid (42 mg., 0.37 mmol) in dry N,N-dimethylformamide (2 ml.) were added 4-dimethylaminopyridine (5 mg.) and benzyl 2-acetamido-2-deoxy-3-O-(D-2-propionyl-L-alanyl-D-isoglutamine benzyl ester)-α-D-glucopyranoside (250 mg., 0.37 mmol). The reaction mixture was cooled in an ice-bath and N,N'-dicyclohexylcarbodiimide (DCC) (77 mg., 0.37 mmol) added. After stirring for 4 hrs. at room temperature, additional 2-furoic acid (42 mg.) and DCC (77 mg.) were added. The reaction mixture was stirred overnight at room temperature. The precipitated solid was filtered and the filtrate evaporated. The residue was taken up in dichloromethane, washed twice with 0.5 M hydrochloric acid and once with saturated aqueous sodium hydrogencarbonate. The organic layer was evaporated to a syrup that was dissolved in the minimal volume of chloroform and the solution applied to a column of silica gel (Merck No. 7734) that was eluted with 17:1 chloroform-methanol. Evaporation of the appropriate fractions gave benzyl 2-acetamido-2-deoxy-6-O-(2-furoyl)-3-O-(D-2-propionyl-L-alanyl-D-isoglutamine benzyl ester)-α-D-glucopyranoside as a syrup that solidified upon trituration with diethyl ether; yield 95 mg. (33%).

The 300-MHz NMR spectrum in dimethylsulfoxide-$d_6$ was in accord with the desired structure.

Step B: 2-acetamido-2-deoxy-6-O-(2-furoyl)-3-O-(D-2-propionyl-L-alanyl-D-isoglutamine)-D-glucose A solution of benzyl 2-acetamido-2-deoxy-6-O-(2-furoyl)-3-O-(D-2-propionyl-L-alanyl-D-isoglutamine benzyl ester)-α-D-glucopyranoside (93 mg.) in glacial acetic acid (5 ml.) was hydrogenolyzed at atmospheric pressure and room temperature in the presence of palladium (added as PdO, 150 mg.). The reaction mixture was filtered through Celite, the filtrate evaporated, and coevaporated several times with water and toluene. The residue was dissolved in the minimal volume of methanol, filtered, and the product precipitated by addition of diethyl ether. The solid was filtered and dried in vacuo over phosphorus pentoxide; yield 60 mg. (85%).

The 300-MHz NMR spectrum in deuterium oxide was in accord with the desired structure.

EXAMPLE 21

Preparation of 2-acetamido-2-deoxy-4,6-di-O-methoxyacetyl-3-O-(D-2-propionyl-L-alanyl-D-isoglutamine)-D-glucose Step A: Preparation of benzyl 2-acetamido-2-deoxy-4,6-di-O-methoxyacetyl-3-O-(D-2-propionyl-L-alanyl-D-isoglutamine benzyl ester)-α-D-glucopyranoside To a solution of methoxyacetic acid (69 μl., 0.90 mmol) in dry N,N-dimethylformamide (3 ml.) were added 4-dimethylaminopyridine (11 mg.) and benzyl 2-acetamido-2-deoxy-3-O-(D-2-propionyl-L-alanyl-D-isoglutamine benzyl ester)-α-D-glucopyranoside (300 mg., 0.45 mmol). After cooling in an ice-bath, N,N'-dicyclohexylcarbodiimide (DCC) (190 mg., 0.92 mmol) was added. After stirring for 4 hrs. at room temperature, additional methoxyacetic acid (69 μl.) and DCC (190 mg.) were added. The reaction mixture was stirred overnight at room temperature, concentrated, the residue taken up in dichloromethane, washed twice with 0.5 M hydrochloric acid, once with saturated sodium hydrogencarbonate, and evaporated. The residue was dissolved in the minimal volume of chloroform and the solution applied to a column of silica gel (Merck No. 7734) that was eluted with 23:1 chloroform-methanol. The fractions containing the desired product were combined and evaporated to give benzyl 2-acetamido-2-deoxy-4,6-di-O-methoxyacetyl-3-O-(D-2-propionyl-L- alanyl-D-isoglutamine benzyl ester)-α-D-glucopyranoside; yield 317 mg. (87%).

The 300-MHz NMR spectrum in dimethylsulfoxide-d$_6$ was in accord with the desired structure.

Step B: Preparation of 2-acetamido-2-deoxy-4,6-di-O-methoxyacetyl-3-O-(D-2-propionyl-L-alanyl-D-isoglutamine)-D-glucose A solution of benzyl 2-acetamido-2-deoxy-4,6-di-O-methoxyacetyl-3-O-(D-2-propionyl-L-alanyl-D-isoglutamine benzyl ester)-α-D-glucopyranoside (225 mg.) in glacial acetic acid (8 ml.) was hydrogenolyzed for 96 hrs. at atmospheric pressure and room temperature in the presence of palladium (two 100 mg. additions as PdO). The catalyst was removed by filtration through Celite, the filtrate was evaporated and coevaporated several times with toluene. The residue was purified by chromatography on a column of silica gel (Merck No. 7734) and elution with 80:20:2 and subsequently with 70:30:3 chloroform-methanol-water. The resulting syrup was dissolved in the minimal volume of methanol and the product was precipitated by addition of diethyl ether. The solid was filtered and dried in vacuo over phosphorus pentoxide; yield 82 mg. (47%).

The 300-MHz NMR spectrum in deuterium oxide was in accord with the desired structure.

EXAMPLE 22

Preparation of 2-acetamido-4,6-di-O-acetamidoacetyl-2-deoxy-3-O-(D-2-propionyl-L-alanyl-D-isoglutamine)-D-glucose Step A: Preparation of benzyl 2-acetamido-4,6-di-O-acetamidoacetyl-2-deoxy-3-O-(D-2-propionyl-L-alanyl-D-isoglutamine benzyl ester)-α-D-glucopyranoside In like manner as Step A in Example 23, substituting a stoichiometric equivalent amount of acetamidoacetic acid for methoxyacetic acid, there was obtained benzyl 2-acetamido-4,6-di-O-acetamidoacetyl-2-deoxy-3-O-(D-2-propionyl-L-alanyl-D-isoglutamine benzyl ester)-α-D-glucopyranoside.

Step B: Preparation of 2-acetamido-4,6-di-O-acetamidoacetyl-2-deoxy-3-O-(D-2-propionyl-L-alanyl-D-isoglutamine)-D-glucose A solution of benzyl 2-acetamido-4,6-di-O-acetamidoacetyl-2-deoxy-3-O-(D-2-propionyl-L-alanyl-D-isoglutamine benzyl ester)-α-D-glucopyranoside (71 mg.) in glacial acetic acid (5 ml.) was hydrogenolyzed for 24 hrs. at atmospheric pressure and room temperature in the presence of palladium (added as PdO, 100 mg.). The catalyst was removed by filtration through Celite, the filtrate evaporated and coevaporated several times with toluene. The residue was dissolved in the minimal volume of methanol and the product precipitated by addition of diethyl ether. The filtered solid was dissolved in a small volume of water and lyophilyzed to afford 2-acetamido-4,6-di-O-acetamidoacetyl-2-deoxy-3-O-(D-2-propionyl-L-alanyl D-isoglutamine)-D-glucose as an amorphous solid, yield 43 mg. (77%).

The 300-MHz NMR spectrum in deuterium oxide was in accord with the desired structure.

EXAMPLE 23

Preparation of 2-acetamido-2-deoxy-6-O-(5-ketohexanoyl)-3-O-(D-2-propionyl-L-alanyl-D-isoglutamine)-D-glucose Step A: Preparation of benzyl 2-acetamido-2-deoxy-6-O-(5-ketohexanoyl)-2-O-(D-2-propionyl-L-alanyl-D-isoglutamine benzyl ester)-α-D-glucopyranoside To a solution of 5-ketohexanoic acid (61 mg., 0.47 mmol) in dry N,N-dimethylformamide (3 ml.) were added 4-dimethylaminopyridine (5.5 mg.) and benzyl 2-acetamido-2-deoxy-3-O-(D-2-propionyl-L-alanyl-D-isoglutamine benzyl ester)-α-D-glucopyranoside (300 mg., 0.45 mmol). After cooling in an ice-bath, N,N'-dicyclohexylcarbodiimide (DCC) (98 mg., 0.47 mmol) was added. After stirring for 5 hrs at room temperature, a second addition of 5-ketohexanoic acid (61 mg.) and DCC (98 mg.) was made. The reaction mixture was stirred overnight at room temperature, the precipitated solid filtered, and the filtrate evaporated. The product was isolated by chromatography on a column of silica gel and elution with 24:1 dichloromethane methanol. Benzyl 2-acetamido-2-deoxy-6-O-(5-ketohexanoyl)-3-O-(D-2-propionyl-L-alanyl-D-isoglutamine benzyl ester)-α-D-glucopyranoside was obtained as a white amorphous solid; yield 213 mg. (61%).

The 300-MHz NMR spectrum in dimethylsulfoxide-d$_6$ was in accord with the desired structure.

Step B: Preparation of 2-acetamido-2-deoxy-6-O-(5-ketohexanoyl)-3-O-(D-2-propionyl-L-alanyl-D-isoglutamine)-D-glucose A solution of benzyl 2-acetamido-2-deoxy-6-O-(5-ketohexanoyl)-3-O-(D-2-propionyl-L-alanyl-D-isoglutamine benzyl ester)-α-D-glucopyranoside (210 mg.) in glacial acetic acid (5 ml.) was hydrogenolyzed for 48 hrs. at atmospheric pressure and room temperature in the presence of palladium (added as PdO, 100 mg.). The catalyst was removed by filtration through Celite, the filtrate evaporated and coevaporated several times with toluene. The residue was taken up in a small volume of ethanol and the product precipitated by addition of diethyl ether. The solid was filtered, dissolved in a small volume of water, and lyophilyzed. 2-Acetamido-2-deoxy-6-O-(5-ketohexanoyl)-3-O-(D-2-propionyl-L-alanyl-D-isoglutamine)-D-glucose was obtained as a white solid; yield 130 mg. (80%).

The 300-MHz NMR spectrum in deuterium oxide was in accord with the desired structure.

What is claimed is:

1. Dipeptidyl 4-O, 6-O-2-amino-2-deoxy-D-glucoses of the general structural formula:

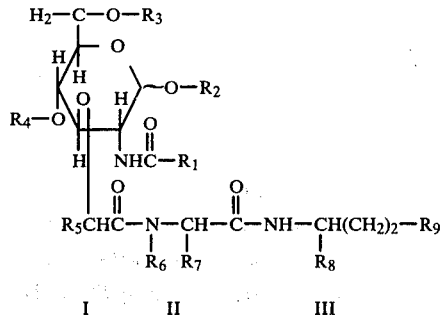

wherein $R_1$ is $C_{1-7}$ alkyl; $C_{1-7}$ alkyl substituted by hydroxy, mercapto, alkoxy of 1-3 carbons, alkyl mercapto of 1-3 carbons, hydroxy or mercapto esterified by an acid of 1-4 carbon atoms, halogen, carboxyl, or carboxyl functionally modified by esterification with a lower alcohol of 1-3 carbons or by amidation; phenyl; or phenyl substituted by one or more alkyl groups of 1-3 carbon atoms or hydroxy or mercapto groups either free or etherified by an alkyl group of 1-3 carbons or esterified by an acid of 1-4 carbons, alkyldioxy of 1-4 carbons, cycloalkyldioxy of 5-7 carbon atoms, amino, or trifluoromethyl;

$R_2$ is hydrogen; $C_{1-7}$ alkyl; $C_{1-7}$ alkyl substitued by hydroxy, mercapto, alkoxy of 1-3 carbons, alkyl mercapto of 1-3 carbons, hydroxy mercapto esterified by an acid of 1-4 carbon atoms, halogen, carboxyl, or carboxyl functionally modified by esterification with a lower alcohol of 1-3 carbons or by amidation; phenyl; phenyl substituted by one or more alkyl groups of 1-3 carbon atoms or hydroxy or mercapto groups either free or etherified by an alkyl group of 1-3 carbons or esterified by an acid of 1-4 carbons, alkyldioxy of 1-4 carbons, cycloalkyldioxy of 5-7 carbon atoms, amino, or trifluoromethyl; phenyl $C_{1-4}$ alkyl; or phenyl $C_{1-4}$ alkyl substituted by one or more alkyl groups of 1-3 carbon atoms or hydroxy or mercapto groups either free or etherified by an alkyl group of 1-3 carbons or esterified by an acid of 1-4 carbons, alkyldioxy of 1-4 carbons, cycloalkyldioxy of 5-7 carbon atoms, amino, or trifluoromethyl;

$R_3$ and $R_4$ may be the same or different and are each independently hydrogen, provided that $R_3$ and $R_4$ may not both be hydrogen; or

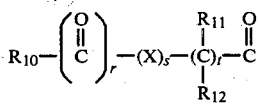

where
X is —O—; —S—; or

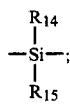

$R_{10}$ is hydrogen; $C_{1-30}$ alkyl; $C_{2-30}$ alkenyl; $C_{1-30}$ alkoxy; phenyl; $C_{1-20}$ alkylsulfonyl; or cholesteryl;

$R_{11}$, $R_{12}$, $R_{14}$, and $R_{15}$ may be the same or different and are each independently hydrogen; $C_{1-20}$ alkyl; $C_{1-20}$ alkylcarbonyloxy; amino; benzyl; $C_{1-20}$ alkoxymethyl; $C_{1-20}$ alkylamido; or

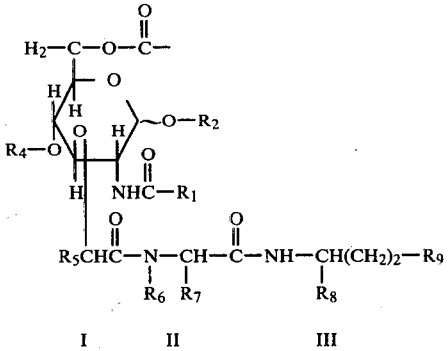

r is 0 or 1; s is 0 or 1; and t is 0 to 20; provided that s may only be 0 when both r and t are greater than 0 or when r is 0 and $R_{10}$ is phenyl; substituted phenyl; 1-adamantyl or heterocycle selected from the group consisting of 2- or 3-furyl, 2- or 3-thienyl, 2- or 3-pyrrolidinyl, 2-, 3- or 4-pyridyl, and 1-tetrazolyl, said heterocycle optionally substituted with $C_{1-20}$ alkylcarbonyl; and where $R_3$ or $R_4$ is other than hydrogen, the other of $R_3$ or $R_4$ may additionally be $C_{1-4}$ alkylcarbonyl; provided further that when r and s are each 0 and $R_{11}$ and $R_{12}$ are each hydrogen, $R_{10}$ is not hydrogen or alkyl;

$R_5$ is hydrogen or $C_{1-10}$ alkyl;

$R_6$ is hydrogen or $R_6$ and $R_7$ taken together are —$(CH_2)_3$—;

$R_7$ is hydrogen; $C_{1-7}$ alkyl; hydroxymethyl; mercaptomethyl; benzyl; or parahydroxybenzyl;

$R_8$ and $R_9$ may be the same or different and are each independently COOR, or CONR'R", where R is hydrogen or $C_{1-7}$ alkyl, and R' and R" are hydrogen or $C_{1-3}$ alkyl; when $R_5$ is $C_{1-10}$ alkyl, the stereochemistry at asymmetric center I is D or L;

when $R_7$ is other than hydrogen, the stereochemistry at asymmetric center II is L; and the stereochemistry at asymmetric center III is D; and acid addition and quaternary salts thereof.

2. A compound according to claim 1 wherein the compound is 2-acetamido-6-O-behenoyloxyisobutyryl-2-deoxy-3-O-(D-2-propionyl-L-alanyl-D-isoglutamine)-D-glucose.

3. A compound according to claim 1 wherein the compound is 2-acetamido-2-deoxy-6-O-(N,O-dipalmitoyl-D,L-seryl)-3-O-(D-2-propionyl-L-alanyl-D-isoglutamine)-D-glucose.

4. A compound according to claim 1 wherein the compound is 2-acetamido-6-O-(adamantane-1-carbonyl)-3-O-(D-2-propionyl-L-alanyl-D-isoglutamine)-D-glucose.

5. A compound according to claim 1 wherein the compound is 2-acetamido-6-O-behenoyloxyacetyl-2-deoxy-3-O-(D-2-propionyl-L-alanyl-D-isoglutamine)-D-glucose.

6. A compound according to claim 1 wherein the compound is 2-acetamido-6-O-[d-2-(3-chloro-4-cyclohexylphenyl)propionyl]-2-deoxy-3-O-(D-2-propionyl-L-alanyl-D-isoglutamine)-D-glucose.

7. A compound according to claim 1 wherein the compound is 2-acetamido-2-deoxy-6-O-(N-palmitoyl-L-prolyl)-3-O-(D-2-propionyl-L-alanyl-D-isoglutamine)-D-glucose.

8. A compound according to claim 1 wherein the compound is 2-Acetamido-2-deoxy-6-O-(2-methyl-2-N- palmitoylamidopropionyl)-3-O-(D-2-propionyl-L-alanyl-D-isoglutamine)-D-glucose.

9. A compound according to claim 1 wherein the compound is 2-acetamido-2-deoxy-6-O-(N-palmitolylglycyl)-3-O-(D-2-propionyl-L-alanyl-D-isoglutamine)-D-glucose.

10. A compound according to claim 1 wherein the compound is 2-acetamido-2-deoxy-6-O-(N-palmitoyl-L-valyl)-3-O-(D-2-propionyl-L-alanyl-D-isoglutamine)-D-glucose.

11. A compound according to claim 1 wherein the compound is 2-acetamido-2-deoxy-6-O-(N-palmitoyl-L-phenylalanyl)-3-O-(D-2-propionyl-L-alanyl-D-isoglutamine)-D-glucose.

12. A compound according to claim 1 wherein the compound is 2-acetamido-2-deoxy-6-O-(N,O-dihexadecyl-D,L-seryl)-3-O-(D-2-propionyl-L-alanyl-D-isoglutamine)-D-glucose.

13. A compound according to claim 1 wherein the compound is 2-acetamido-2-deoxy-6-O-(D,L-2-palmitamidopalmitoyl)-3-O-(D-2-propionyl-L-alanyl-D-isoglutamine)-D-glucose.

14. A compound according to claim 1 wherein the compound is 2-acetamido-2-deoxy-6-O-(N,N'-dipalmitoyl-L-lysyl)-3-O-(D-2-propionyl-L-alanyl-D-isoglutamine)-D-glucose.

15. A compound according to claim 1 wherein the compound is 2-acetamido-2-deoxy-6-O-(N-hexadecanesulfonylglycyl)-3-O-(D-2-propionyl-L-alanyl-D-isoglutamine)-D-glucose.

16. A compound according to claim 1 wherein the compound is bis(6-O-muramyl dipeptide)O-palmitoyltartronate.

17. A compound according to claim 1 wherein the compound is 2-acetamido-6-O-cholesteryloxycarbonyl-2-deoxy-3-O-(D-2-propionyl-L-alanyl-D-isoglutamine)-D-glucose.

18. A compound according to claim 1 wherein the compound is methyl 2-acetamido-2-deoxy-6-O-hexadecyloxycarbonyl-3-O-(D-2-propionyl-L-alanyl-D-isoglutamine)-β-D-glucose.

19. A compound according to claim 1 wherein the compound is methyl 2-acetamido-6-O-behenoylisobutyryl-2-deoxy-3-O-(D-2-propionyl-L-alanyl-D-isoglutamine)-β-D-glucose.

20. A compound according to claim 1 wherein the compound is 2-acetamido-2-deoxy-6-O-(16-hydroxyhexadecanoyl)-3-O-(D-2-propionyl-L-alanyl-D-isoglutamine)-D-glucose.

21. A compound according to claim 1 wherein the compound is 2-acetamido-6-O-(16-acetoxyhexadecanoyl)-4-O-acetyl-3-O-(D-2-propionyl-L-alanyl-D-isoglutamine)-D-glucose.

22. A compound according to claim 1 wherein the compound is 2-acetamido-2-deoxy-6-O-(2-furoyl)-3-O-(D-2-propionyl-L-alanyl-D-isoglutamine)-D-glucose.

23. A compound according to claim 1 wherein the compound is 2-acetamido-2-deoxy-4,6-di-O-methoxyacetyl-3-O-(D-2-propionyl-L-alanyl-D-isoglutamine)-D-glucose.

24. A compound according to claim 1 wherein the compound is 2-acetamido-4,6-di-O-acetamidoacetyl-2-deoxy-3-O-(D-2-propionyl-L-alanyl-D-isoglutamine)-D-glucose.

25. A compound according to claim 1 wherein the compound is 2-acetamido-2-deoxy-6-O-(5-ketohexanoyl)-3-O-(D-2-propionyl-L-alanyl-D-isoglutamine)-D-glucose.

26. A compound according to claim 1 wherein the compound is 2-acetamido-6-O-(6-aminohexanoyl)-2-deoxy-3-O-(D-2-propionyl-L-alanyl-D-isoglutamine)-D-glucose.

27. A compound according to claim 1 wherein the compound is 2-acetamido-6-O-(6-acetamidohexanoyl)-2-deoxy-3-O-(D-2-propionyl-L-alanyl-D-isoglutamine)-D-glucose.

28. A compound according to claim 1 wherein the compound is 2-acetamido-2-deoxy-6-O-(phenylacetyl)-3-O-(D-2-propionyl-L-alanyl-D-isoglutamine)-D-glucose.

29. A compound according to claim 1 wherein the compound is 2-acetamido-2-deoxy-6-O-(phenoxyacetyl)-3-O-(D-2-propionyl-L-alanyl-D-isoglutamine)-D-glucose.

30. A compound according to claim 1 wherein the compound is 2-acetamido-2-deoxy-6-O-(ethoxycarbonyl)-3-O-(D-2-propionyl-L-alanyl-D-isoglutamine)-D-glucose.

31. A compound according to claim 1 wherein the compound is 2-acetamido-2-deoxy-6-O-(1-tetrazolylacetyl)-3-O-(D-2-propionyl-L-alanyl-D-isoglutamine)-D-glucose.

32. An antibacterial composition comprising a physiologically acceptable medium and an antibacterially effective amount of a compound of claim 1.

33. A vaccine against bacterial, viral, or parasitic infections or against various tissue antigens of normal or pathogenic origin comprising a compound of claim 1 in an amount effective to impart an immunostimulatory response.

34. A composition comprising a compound of claim 1 in an amount effective to impart an immunostimulatory response and a physiologically acceptable medium.

* * * * *